United States Patent
Kikuchi et al.

Patent Number: 5,753,654
Date of Patent: May 19, 1998

[54] DIAMINOMETHYLIDENE DERIVATIVES

[75] Inventors: Haruhiko Kikuchi; Hiroaki Satoh; Ruta Fukutomi; Kohei Inomata; Masashi Suzuki; Koichiro Hagihara; Takeo Arai; Setsuko Mino; Haruko Eguchi, all of Ohimachi, Japan

[73] Assignee: Nisshin Flour Milling Co., Ltd., Tokyo, Japan

[21] Appl. No.: 737,133

[22] PCT Filed: May 17, 1995

[86] PCT No.: PCT/JP95/00938

§ 371 Date: Nov. 7, 1996

§ 102(e) Date: Nov. 7, 1996

[87] PCT Pub. No.: WO95/31431

PCT Pub. Date: Nov. 23, 1995

[30] Foreign Application Priority Data

May 18, 1994 [JP] Japan ................. 6-103570

[51] Int. Cl.$^6$ ............ A61K 31/535; C07D 265/36; C07D 413/00; C07D 265/30
[52] U.S. Cl. ............. 514/230.5; 544/105; 544/121; 544/162
[58] Field of Search ................. 544/105, 121, 544/162; 514/230.5

[56] References Cited

U.S. PATENT DOCUMENTS

| | | | |
|---|---|---|---|
| 3,585,142 | 6/1971 | Muzyczko et al. | 252/87 |
| 5,422,373 | 6/1995 | Franzmann | 514/598 |
| 5,621,010 | 4/1997 | Sueda et al. | 514/596 |

*Primary Examiner*—Mukund J. Shah
*Assistant Examiner*—Tamthom T. Ngo
*Attorney, Agent, or Firm*—Oblon, Spivak, McClelland, Maier & Neustadt, P.C.

[57] ABSTRACT

Novel diaminomethylidene derivatives represented by formula (I)

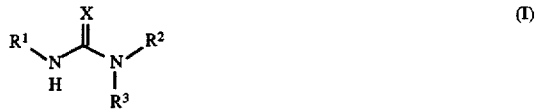

wherein
$R^1$ is a hydrogen atom, a $C_1$-$C_6$ alkyl group, a $C_3$-$C_6$ cycloalkyl group and others, $R^2$ is a group of the following formula

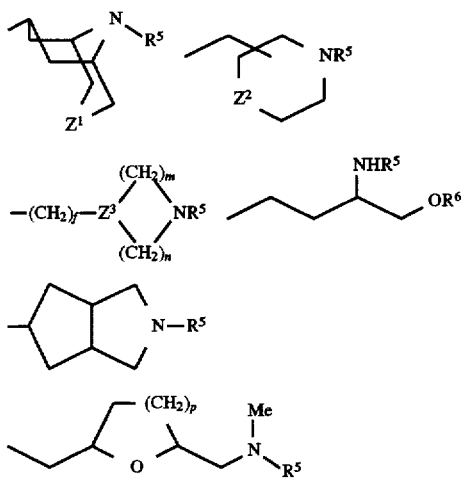

and others, $R^3$ is a hydrogen atom, a $C_1$-$C_6$ alkyl group and others, X is O, S, CHNO$_2$, C(COOR$^4$)$_2$, C(COOR$^4$)CN or C(CN)$_2$) or pharmacologically acceptable salts thereof.

The above-mentioned compounds are useful as a gastrointestinal prokinetic agent to be used for the treatment of digestive tract diseases.

5 Claims, No Drawings

DIAMINOMETHYLIDENE DERIVATIVES

This is a 371 application of PCT/JP 95/00938 filed on May 17, 1995 published as WO95/31431 Nov. 23, 1995.

1. Technical Field

This invention relates to novel diaminomethylidene derivatives and pharmacologically acceptable acid addition salts and quaternary ammonium salts thereof.

More specifically, this invention relates to new diaminomethylidene derivatives having a promoting action of the release of acetylcholine in digestive tracts, thus being useful for the treatment of digestive tract disorders derived from chronic gastritis, diabetes mellitus, post-gastrectomy and peptic ulcer and digestive tract diseases including reflux esophagitis, irritable bowel syndrome and spurious ileus, as well as a gastrointestinal prokinetic agent which comprises as an active ingredient the said derivatives.

2. Background Art

The abnormality in function of a gastrointestinal mobility by various causes such as chronic gastritis, diabetes, post-gastrectomy, peptic ulcer and others could result in the reflux of the gastric content into the esophagus, delayed emptying of the gastric content and the depressed function of the small and large intestines.

This can lead to appearances of nausea, vomiting, heartburn, anorexia, abdominal distention, epigastric dysphoria, abdominaglia, constipation and further reflux esophagitis. One cause of the diseases such as irritable bowel syndrome and spurious ileus has been considered to be the depression in gastrointestinal motility.

The agents for the treatment of these conditions and diseases include direct cholinergic agent (e.g. Aclatonium Napadisilate) or Dopamine antagonist (e.g. Doperidone). However, it is well-known that these known agents have the problems in their effects and side-effects, which may include, for example, diarrhea and extrapyramidal syndrome.

It is well-known that acetylcholine is the neurotransmitter participating in the control of gastrointestinal motility. Accordingly, it may be considered that a compound capable of promoting the release of acetylcholine in digestive tract may be a gastrointestinal prokinetic agent showing far more effectiveness and less side effects. In view of this, it has been desired to find out such a type of compounds and develop a process for obtaining them.

DISCLOSURE OF INVENTION

The present inventors have made earnest studies to solve these problems and, as a result, have found that the diaminomethylidene derivatives as defined below can exert a remarkable promoting action of the release of acetylcholine, upon which this invention has been completed.

More particularly, this invention is concerned with a diaminomethylidene derivative represented by formula (I)

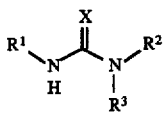

(I)

wherein $R^1$ is a hydrogen atom, a $C_1$–$C_6$ alkyl group, a $C_3$–$C_6$ cycloalkyl group, a $C_3$–$C_6$ cycloalkyl $C_1$–$C_4$ alkyl group, an aryl group or an aryl $C_1$–$C_4$ alkyl group, in which the aryl moiety of the aryl group or aryl $C_1$–$C_4$ alkyl group may be optionally substituted with a halogen atom, a $C_1$–$C_6$ alkyl group, a halo $C_1$–$C_6$ alkyl group, a $C_1$–$C_6$ alkoxy group, a $C_1$–$C_6$ alkoxycarbonyl group, a phenyl group or an amino group, X is O, S, CHNO$_2$, C(COOR$^4$)$_2$, C(COOR$^4$)CN or C(CN)$_2$, in which $R^4$ is a $C_1$–$C_6$ alkyl group, a $C_3$–$C_6$ cycloalkyl group, an aryl group, or an aryl $C_1$–$C_4$ alkyl group, $R^2$ is a group of the following formulae (II)–(IX)

(II)

(III)

(IV)

(V)

(VI)

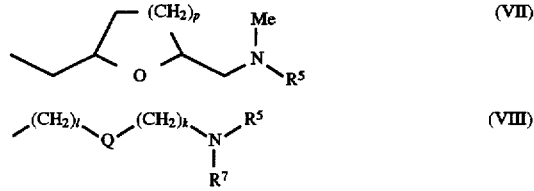

(VII)

(VIII)

(IX)

wherein $R^5$ is a $C_1$–$C_6$ alkyl group, an aryl $C_1$–$C_4$ alkyl group, a heteroaryl $C_1$–$C_4$ alkyl group, an aryloxy $C_2$–$C_6$ alkyl group, or a pyrrolidinylcarbonyl $C_1$–$C_4$ alkyl group, in which the aryl moiety of the said groups may be optionally substituted with a halogen atom, a $C_1$–$C_6$ alkyl group, a halo $C_1$–$C_6$ alkyl group, a $C_1$–$C_6$ alkoxy group, a $C_1$–$C_6$ alkoxycarbonyl group, a phenyl group or an amino group, $R^6$ is a hydrogen atom, a $C_1$–$C_6$ alkyl group, an aryl group or an aryl $C_1$–$C_4$ alkyl group, $Z^1$ and $Z^2$ are O, S, N($C_1$–$C_4$ alkyl) or CH$_2$ and $Z^3$ is N or CH, l is 0–2, n is 4 when m is 0, n is 1 or 3 when m is 1, n is 2 when m is 2, p is 1–2, j is 0–3, k is 0–3, a sum of j and k is 1–6, h is 1–6, Q is O, NR$^8$, CHOR$^9$ or OCH$_2$ CH$_2$, $R^7$ and $R^8$ may be the same or different and each is a hydrogen atom, a $C_1$–$C_6$ alkyl group or a $C_1$–$C_4$ alkoxy $C_2$–$C_4$ alkyl group, $R^9$ is a hydrogen atom or a $C_1$–$C_6$ alkyl group, $R^3$ is a hydrogen atom, a $C_1$–$C_6$ alkyl group or a $C_1$–$C_6$ alkoxy $C_2$–$C_6$ alkyl group, or $R^2$ and $R^3$ may represent, together with the nitrogen atom to which they are attached, a N-substituted piperazine ring of the following formula (X)

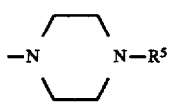

(X)

wherein $R^5$ represents the groups as defined above; provided that there is excluded a compound wherein $R^1$ is an aryl group, X is O, and $R^2$ is a group of formula (II) wherein $R^5$ is a $C_1$–$C_2$ alkyl group or a pharmacologically acceptable salt thereof.

In formula (I) for the diaminomethylidene derivatives of this invention, the $C_1$–$C_6$ alkyl group represented by $R^1$ may include methyl, ethyl, n-propyl, isopropyl, n-butyl, isobutyl, n-pentyl, neo-pentyl, n-hexyl and the like; the $C_3$–$C_6$ cycloalkyl group may include cyclopropyl, cyclopentyl or cyclohexyl; the aryl group may include phenyl, naphthyl, o-fluorophenyl, m-fluorophenyl, p-fluorophenyl, o-chlorophenyl, m-chlorophenyl, p-chlorophenyl, 3,4-dichlorophenyl, o-methylphenyl, m-methylphenyl, p-methylphenyl, o-ethylphenyl, m-ethylphenyl, p-ethylphenyl, o-methoxyphenyl, m-methoxyphenyl, p-methoxyphenyl, o-ethoxyphenyl, m-ethoxyphenyl, p-ethoxyphenyl, 3,4-dimethoxyphenyl, o-methoxycarbonylphenyl, m-methoxycarbonylphenyl, p-methoxycarbonylphenyl, o-aminophenyl, m-aminophenyl, p-aminophenyl and the like; the $C_3$–$C_6$ cycloalkyl $C_1$–$C_4$ alkyl group may include cyclopropylmethyl, cyclohexylmethyl and the like; the aryl $C_1$–$C_4$ alkyl group may include benzyl, phenethyl, o-fluorobenzyl, m-fluorobenzyl, p-fluorobenzyl, o-chlorobenzyl, m-chlorobenzyl, p-chlorobenzyl, 3,4-dichlorobenzyl, o-methylbenzyl, m-methylbenzyl, p-methylbenzyl, o-trifluoromethylbenzyl, m-trifluoromethylbenzyl, p-trifluoromethylbenzyl, o-methoxybenzyl, m-methoxybenzyl, p-methoxybenzyl, 3,4-dimethoxybenzyl, o-methoxycarbonylbenzyl, m-methoxycarbonylbenzyl, p-methoxycarbonylbenzyl, biphenyl-2-ylmethyl, biphenyl-3-ylmethyl, biphenyl-4-ylmethyl, o-aminobenzyl, m-aminobenzyl, p-aminobenzyl, o-fluorophenethyl, m-fluorophenethyl, p-fluorophenethyl, o-chlorophenethyl, m-chlorophenethyl, p-chlorophenethyl, 3,4-dichlorophenethyl, o-methylphenethyl, m-methylphenethyl, p-methylphenethyl, o-trifluoromethylphenethyl, m-trifluoromethylphenethyl, p-trifluoromethylphenethyl, o-methoxyphenethyl, m-methoxyphenethyl, p-methoxyphenethyl, 3,4-dimethoxyphenethyl, o-methoxycarbonylphenethyl, m-methoxycarbonylphenethyl, p-methoxycarbonylphenethyl, 2-(biphenyl-2-yl)ethyl, 2-(biphenyl-3-yl)ethyl, 2-(biphenyl-4-yl)ethyl, o-aminophenethyl, m-aminophenethyl, p-aminophenethyl and the like; the $C_1$–$C_6$ alkyl group represented by $R^4$ may include methyl, ethyl, n-propyl, isopropyl, n-butyl, isobutyl, n-pentyl, neo-pentyl, n-hexyl and the like; the $C_3$–$C_6$ cycloalkyl group may include cyclopropyl, cyclopentyl, cyclohexyl and the like; the aryl group may include phenyl, naphthyl and the like; the aryl $C_1$–$C_4$ alkyl group may include benzyl, phenethyl and the like; the $C_1$–$C_6$ alkyl group represented by $R^3$ may include methyl, ethyl, n-propyl, isopropyl, n-butyl, isobutyl, n-pentyl, neo-pentyl, n-hexyl and the like; the $C_1$–$C_6$ alkoxy $C_2$–$C_6$ alkyl group may include 2-methoxyethyl, 2-ethoxyethyl and the like.

The $C_1$–$C_6$ alkyl group represented by $R^5$ in formulae (II)–(X) may include methyl, ethyl, n-propyl, isopropyl, n-butyl, isobutyl, n-pentyl, neo-pentyl, n-hexyl and the like; the aryl $C_1$–$C_4$ alkyl group may include benzyl, phenethyl, o-fluorobenzyl, m-fluorobenzyl, p-fluorobenzyl, o-chlorobenzyl, m-chlorobenzyl, p-chlorobenzyl, 3,4-dichlorobenzyl, o-methylbenzyl, m-methylbenzyl, p-methylbenzyl, o-trifluoromethylbenzyl, m-trifluoromethylbenzyl, p-trifluoromethylbenzyl, o-methoxybenzyl, m-methoxybenzyl, p-methoxybenzyl, 3,4-dimethoxybenzyl, o-methoxycarbonylbenzyl, m-methoxycarbonylbenzyl, p-methoxycarbonylbenzyl, biphenyl-2-ylmethyl, biphenyl-3-ylmethyl, biphenyl-4-ylmethyl, o-aminobenzyl, m-aminobenzyl, p-aminobenzyl, o-fluorophenethyl, m-fluorophenethyl, p-fluorophenethyl, o-chlorophenethyl, m-chlorophenethyl, p-chlorophenethyl, 3,4-dichlorophenethyl, o-methylphenethyl, m-methylphenethyl, p-methylphenethyl, o-trifluoromethylphenethyl, m-trifluoromethylphenethyl, p-trifluoromethylphenethyl, o-methoxyphenethyl, m-methoxyphenethyl, p-methoxyphenethyl, 3,4-dimethoxyphenethyl, o-methoxycarbonylphenethyl, m-methoxycarbonylphenethyl, p-methoxycarbonylphenethyl, 2-(biphenyl-2-yl)ethyl, 2-(biphenyl-3-yl)ethyl, 2-(biphenyl-4-yl)ethyl, o-aminophenethyl, m-aminophenethyl, p-aminophenethyl and the like; the heteroaryl $C_1$–$C_4$ alkyl group may include 2-pyridylmethyl, 3-pyridylmethyl, 4-pyridylmethyl, 1H-indol-3-ylethyl and the like; the aryloxy $C_2$–$C_6$ alkyl group may include phenoxy-2-ethyl, phenoxy-3-propyl, 2-fluorophenoxy-3-propyl, 3-fluorophenoxy-3-propyl, 4-fluorophenoxy-3-propyl, 2-chlorophenoxy-3-propyl, 3-chlorophenoxy-3-propyl, 4-chlorophenoxy-3-propyl, 3,4-dichlorophenoxy-3-propyl and the like; the pyrrolidinylcarbonyl $C_1$–$C_4$ alkyl group may include pyrrolidinylcarbonylmethyl group and the like.

The $C_1$–$C_6$ alkyl group represented by $R^6$ may include methyl, ethyl, n-propyl, isopropyl, n-butyl, isobutyl, n-pentyl, neo-pentyl, n-hexyl and the like; the aryl $C_1$–$C_4$ alkyl group may include benzyl, phenethyl and the like, and the aryl group may include phenyl or naphthyl and the like.

The $C_1$–$C_6$ alkyl group in the $N(C_1$–$C_6$ alkyl) group for $Z^1$ and $Z^2$ may include methyl, ethyl, n-propyl, isopropyl, n-butyl, isobutyl, n-pentyl, neo-pentyl, n-hexyl and the like.

The $C_1$–$C_6$ alkyl group represented by $R^7$ and $R^8$ may include methyl, ethyl, n-propyl, isopropyl, n-butyl, isobutyl, n-pentyl, neo-pentyl, n-hexyl and the like; the $C_1$–$C_4$ alkoxy $C_2$–$C_4$ alkyl group may include methoxyethyl, ethoxyethyl and the like.

The $C_1$–$C_6$ alkyl group represented by $R^9$ may include methyl, ethyl, n-propyl, isopropyl, n-butyl, isobutyl, n-pentyl, neo-pentyl, n-hexyl and the like.

The compounds represented by formula (I) of this invention may be prepared according to the process as explained below.

That is to say, the compound represented by formula (I) may be prepared by reacting a methylthioaminomethylidene compound represented by formula (XI)

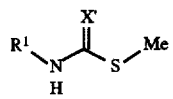

(XI)

wherein $R^1$ has the same meaning as above and X' is $CHNO_2$, $C(COOR^4)_2$, $C(COOR^4)CN$ or $C(CN)_2$, and $R^4$ is a $C_1$–$C_6$ alkyl group, a $C_3$–$C_6$ cycloalkyl group, an aryl group or an aryl $C_1$–$C_4$ alkyl group, with an amino compound represented by formula (XII)

$R^2R^3NH$ (XII)

wherein $R^2$ and $R^3$ have the same meanings as above.

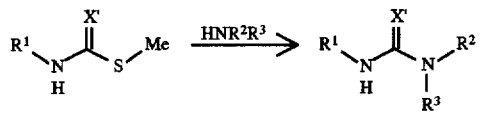

wherein $R^2$ and $R^3$ have the same meanings as above.

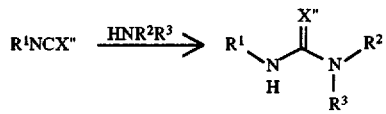

Examples of the methylthioaminomethylidene compounds may illustratively include 2-benzylamino-2-methylthio-1,1-ethylenedicarbonitrile, 2-methylamino-2-methylthio-1,1-ethylenedicarbonitrile, 2-phenylamino-2-methylthio-1,1-ethylenedicarbonitrile, 2-cyclohexylamino-2-methylthio-1,1-ethylenedicarbonitrile, 2-isobutylamino-2-methylthio-1,1-ethylenedicarbonitrile, ethyl 3-cyclohexylamino-3-methylthio-2-cyanoacrylate, ethyl 2-cyano-3-methylamino-3-methylthioacrylate, ethyl 2-cyano-3-phenylamino-3-methylthioacrylate, ethyl 2-cyano-3-isobutylamino-3-methylthioacrylate, ethyl 3-benzylamino-2-cyano-3-methylthioacrylate, ethyl 2-cyano-3-(p-methoxyphenyl)amino-3-methylthioacrylate, N-(1-methylthio-2-nitrovinyl)-N-methylamine, 2-[4-(p-fluorobenzyl)-2-morpholinylmethylamino]-2-methylthio-1,1-ethylenedicarbonitrile and the like.

Examples of the amino compounds may illustratively include 2-aminomethyl-4-(p-fluorobenzyl)morpholine, 1-(p-fluorobenzyl)piperazine, tert-butoxy N-(5-amino-3-oxapentyl)-N-(p-fluorobenzyl)carbamate, p-fluorobenzylamine, endo-7-amino-9-(p-fluorobenzyl)-9-aza-3-oxabicyclo[3.3.1]nonane, endo-7-amino-9-[3-(p-fluorophenoxypropyl)]-9-aza-3-oxabicyclo[3.3.1]nonane and the like.

The reaction of the aminomethylidene compound with the amino compound may be carried out using an amount of the amino compound of 0.2–5 moles, preferably 0.5–2 moles, per mole of the methylthioaminomethylidene compound. The reaction may be preferably carried out in an organic solvent at a temperature ranging from 78° C. to a boiling point of the solvent used, and the reaction may proceed very easily so that the reaction may proceed usually at a temperature from room temperature to about 45° C. under warming. The organic solvent which may be employed herein may include dimethylformamide, acetonitrile, dimethyl sulfoxide, acetone, ethyl acetate, ether, chloroform, methylene chloride, tetrahydrofuran, dioxane, toluene, benzene and the like and dimethylformamide or acetonitrile may be preferably used.

The desired product thus prepared may be isolated and purified from the reaction mixture by way of well-known purification means such as concentration, extraction, chromatographic purification, recrystallization and others.

Further, the compounds represented by formula (I) wherein X is O or S may be prepared by the reaction of an isocyanate or isothiocyanate compound represented by formula (XIII)

$$R^1NCX''$$ (XIII)

wherein $R^1$ has the same meaning as above and X" is O or S, with an amino compound represented by formula (XII)

$$R^2R^3NH$$ (XII)

Examples of the isocyanate compounds may illustratively include phenyl isocyanate, methyl isocyanate, benzyl isocyanate, cyclohexyl isocyanate, isobutyl isocyanate, p-methoxyphenyl isocyanate and the like. Examples of the isothiocyanate compounds may illustratively include phenyl isothiocyanate, methyl isothiocyanate, benzyl isothiocyanate, cyclohexyl isothiocyanate, isobutyl isothiocyanate, p-methoxyphenyl isothiocyanate and the like.

Examples of the amino compounds may illustratively include 2-aminomethyl-4-(p-fluorobenzyl)morpholine, 1-(p-fluorobenzyl)piperazine, tert-butoxy N-(5-amino-3-oxapentyl)-N-(p-fluorobenzyl)carbamate, p-fluorobenzylamine, endo-7-amino-9-(p-fluorobenzyl)-9-aza-3-oxabicyclo[3.3.1]nonane, endo-7-amino-9-[3-(p-fluorophenoxypropyl)]-9-aza-3-oxabicyclo[3.3.1]nonane and the like.

The reaction of the isocyanate or isothiocyanate compound with the amino compound may be carried out using an amount of the amino compound of 0.2–5 moles, preferably 0.5–2 moles, per mole of the isocyanate or isothiocyanate compound. The reaction may be preferably carried out in an organic solvent at a temperature ranging from room temperature to a boiling point of the solvent used, and the reaction may proceed very easily so that the reaction may be proceed usually at a temperature from room temperature to about 45° C. by under slightly warming. The organic solvent which may be employed may include dimethylformamide, acetonitrile, dimethylsulfoxide, acetone, ethyl acetate, ether, chloroform, methylene chloride, tetrahydrofuran, dioxane, toluene, benzene and the like and dimethylformamide or acetonitrile may be preferably used. Illustrative compounds of the present invention may be given below in terms of their chemical names;

2-benzylamino-2-[4-(p-fluorobenzyl)-2-morpholinylmethylamino]-1,1-ethylenedicarbonitrile, 2-cyclohexylamino-2-[4-(p-fluorobenzyl)-2-morpholinylmethylamino]-1,1-ethylenedicarbonitrile, 2-[4-(p-fluorobenzyl)-2-morpholinylmethylamino]-2-phenylamino-1,1-ethylenedicarbonitrile, 2-[4-(p-fluorobenzyl)-2-morpholinylmethylamino]-2-methylamino-1,1-ethylenedicarbonitrile, 2-cyclohexylamino-2-[4-(p-fluorobenzyl)-1,-piperazinyl]-1,1-ethylenedicarbonitrile, 2-benzylamino-2-[4-(p-fluorobenzyl)-1-piperazinyl]-1,1-ethylenedicarbonitrile, 2-[4-(p-fluorobenzyl)-2-morpholinylmethylamino]-2-isobutylamino-1,1-ethylenedicarbonitrile, ethyl 3-benzylamino-3-[4-(p-fluorobenzyl)-2-morpholinylmethylamino]-2-cyanoacrylate, ethyl 3-[4-(p-fluorobenzyl)-2-morpholinylmethylamino]-3-phenylamino-2-cyanoacrylate, ethyl 3-[4-(p-fluorobenzyl)-2-morpholinylmethylamino]-3-isobutylamino-2-cyanoacrylate, ethyl 3-cyclohexylamino-3-[4-(p-fluorobenzyl)-2-morpholinylmethylamino]-2-cyanoacrylate, ethyl 3-[4-(p-fluorobenzyl)-2-morpholinylmethylamino]-3-(p-methoxybenzyl)amino-2-cyanoacrylate, ethyl 3-[4-(p-fluorobenzyl)-2-morpholinylmethylamino]-3-methylamino-2-cyanoacrylate, ethyl 3-cyclohexylamino-3-[7-(p-fluorophenyl)-6-aza-3-oxaheptylamino]-2-cyanoacrylate,
ethyl 3-benzylamino-3-[4-(p-fluorobenzyl)-1-piperizinyl]-2-cyanoacrylate,
2-(p-fluorobenzylamino)-2-[4-(p-fluorobenzyl)-2-morpholinylmethylamino]-1,1-ethylenedicarbonitrile,
ethyl 2-cyano-3-[endo-9-(p-fluorobenzyl)-9-aza-3-oxabicyclo[3.3.1]non-7-ylamino]-3-methylaminoacrylate,
2-[endo-9-(p-fluorobenzyl)-9-aza-3-oxabicyclo[3.3.1]non-7-ylamino]-2-methylamino-1,1-ethylenedicarbonitrile,
2-[endo-9-[3-(p-fluorophenoxy)propyl]-9-aza-3-oxabicyclo[3.3.1]non-7-ylamino]-2-methylamino-1,1-ethylenedicarbonitrile,
N-[endo-9-(p-fluorobenzyl)-9-aza-3-oxabicyclo[3.3.1]non-7-yl]-N'-methyl-2-nitrovinylidene-1,1-diamine,
1-[4-(p-fluorobenzyl)-2-morpholinylmethyl]-3-phenylurea,
1-[4-(p-fluorobenzyl)-2-morpholinylmethyl]-3-methylurea,
1-[endo-9-(p-fluorobenzyl)-9-aza-3-oxabicyclo[3.3.1]non-7-yl]-3-methylurea,
2-[4-(p-chlorobenzyl)-2-morpholinylmethylamino]-2-methylamino-1,1-ethylenedicarbonitrile,
2-[4-(3,4-dichlorobenzyl)-2-morpholinylmethylamino]-2-methylamino-1,1-ethylenedicarbonitrile,
2-[4-(p-trifluoromethylbenzyl)-2-morpholinylmethylamino]-2-methylamino-1,1-ethylenedicarbonitrile,
2-(4-benzyl-2-morpholinylmethylamino)-2-methylamino-1,1-ethylenedicarbonitrile,
2-methylamino-2-[4-(4-pyridylmethyl)-2-morpholinylmethylamino]-1,1-ethylenedicarbonitrile,
2-[4-(biphenyl-4-ylmethyl)-2-morpholinylmethylamino]-2-methylamino-1,1-ethylenedicarbonitrile,
2-[4-(p-methoxybenzyl)-2-morpholinylmethylamino]-2-methylamino-1,1-ethylenedicarbonitrile,
2-[4-(p-fluorobenzyl)-3-morpholinylmethylamino]-2-methylamino-1,1-ethylenedicarbonitrile,
2-[1-(p-fluorobenzyl)-3-piperidinylmethylamino]-2-methylamino-1,1-ethylenedicarbonitrile,
2-[1-(p-methoxybenzyl)-3-piperidinylmethylamino]-2-methylamino-1,1-ethylenedicarbonitrile,
2-[1-(3,4-dimethoxybenzyl)-3-piperidinylmethylamino]-2-methylamino-1,1-ethylenedicarbonitrile,
2-[1-(p-methoxycarbonylbenzyl)-3-piperidinylmethylamino]-2-methylamino-1,1-ethylenedicarbonitrile,
2-methylamino-2-[1-(4-pyridylmethyl)-3-piperidinylmethylamino]-1,1-ethylenedicarbonitrile,
2-[1-(p-trifluoromethylbenzyl)-3-piperidinylmethylamino]-2-methylamino-1,1-ethylenedicarbonitrile,
2-[1-(p-chlorobenzyl)-3-piperidinylmethylamino]-2-methylamino-1,1-ethylenedicarbonitrile,
2-[1-(3,4-dichlorobenzyl)-3-piperidinylmethylamino]-2-methylamino-1,1-ethylenedicarbonitrile,
2-[endo-9-(p-fluorobenzyl)-9-aza-3-oxabicyclo[3.3.1]non-7-ylamino]-2-methylamino-1,1-ethylenedicarbonitrile,
2-methylamino-2-(endo-3,9-dimethyl-3,9-diazabicyclo[3.3.1]-non-7-ylamino)-1,1-ethylenedicarbonitrile,
2-methylamino-2-(endo-9-methyl-9-aza-3-oxabicyclo[3.3.1]non-7-ylamino)-1,1-ethylenedicarbonitrile,
2-[exo-9-(p-fluorobenzyl)-9-aza-3-oxabicyclo[3.3.1]non-7-ylamino]-2-methylamino-1,1-ethylenedicarbonitrile,
2-[1-(p-fluorobenzyl)-3-azetidinylamino]-2-methylamino-1,1-ethylenedicarbonitrile,
2-[1-(p-fluorobenzyl)-4-piperidinylamino]-2-methylamino-1,1-ethylenedicarbonitrile,
2-[4-(p-fluorobenzyl)-1-piperazinyl]-2-methylamino-1,1-ethylenedicarbonitrile,
2-[2-[4-(p-fluorobenzyl)-1-piperazinyl]ethylamino]-2-methylamino-1,1-ethylenedicarbonitrile,
2-[N-[2-[1-(p-fluorobenzyl)-2-piperidyl]ethyl]-N-methylamino]-2-methylamino-1,1-ethylenedicarbonitrile,
2-[1-(p-fluorobenzyl)-4-piperidinylmethylamino]-2-methylamino-1,1-ethylenedicarbonitrile,
2-[1-(p-fluorobenzyl)-2-piperidylmethylamino]-2methylamino-1,1-ethylenedicarbonitrile,
2-methylamino-2-[4-[2-oxo-2-(1-pyrrolidinyl)ethyl]-1-piperazinyl]-1,1-ethylenedicarbonitrile,
2-[4-benzyloxy-3-(p-fluorobenzylamino)butylamino]-2-methylamino-1,1-ethylenedicarbonitrile,
2-[2-(p-fluorobenzyl)-3aβ,5α,6aβ-octahydrocyclopenta[c]pyrrol-5-amino]-2-methylamino-1,1-ethylenedicarbonitrile,
2-[5-(p-fluorophenyl)-2-hydroxy-4-azapentylamino]-2-methylamino-1,1-ethylenedicarbonitrile,
2-[N-[5-p-fluorophenyl-4-(2-methoxyethyl)-4-azapentyl]-N-(2-methoxyethyl)amino]-2-methylamino-1,1-ethylenedicarbonitrile,
2-[4-(p-fluorobenzyl)-4-aza-7-oxaoctylamino]-2-methylamino-1,1-ethylenedicarbonitrile,
2-[cis-6-[N-(p-fluorobenzyl)-N-methylaminomethyl]-2-tetrahydropyranylmethylamino]-2-methylamino-1,1-ethylenedicarbonitrile,
2-[trans-6-[N-(p-fluorobenzyl)-N-methylaminomethyl]-2-tetrahydropyranylmethylamino]-2-methylamino-1,1-ethylenedicarbonitrile,
2-[trans-5-[N-(p-fluorobenzyl)-N-methylaminomethyl]-2-tetrahydrofuranylmethylamino]-2-methylamino-1,1-ethylenedicarbonitrile,
2-[cis-5-[N-(p-fluorobenzyl)-N-methylaminomethyl]-2-tetrahydrofuranylmethylamino]-2-methylamino-1,1-ethylenedicarbonitrile.

The compounds of the present invention as described above have a remarkable gastrointestinal prokinetic action, thus being useful as a therapeutic agent for digestive tract diseases, as will be proved in the following Examples.

The present compounds represented by formula (I) may be converted, if desired, to the corresponding acid addition salts with pharmaceutically acceptable acids. The acid addition salts are included within the scope of this invention, which include, for example, the salts with inorganic acids such as hydrochloric acid, hydrobromic acids, sulfuric acid, nitric acid, phosphoric acid and the like, or the salts with organic acids such as acetic acid, succinic acid, oxalic acid, malic acid, tartaric acid and the like.

The compounds represented by formula (I) when they are to be applied as medicines may be formulated to various dosage forms. More specifically, the preparations thus formed may be administered orally in a dosage form of tablets, sugar-coated tablets, hard capsules, soft capsules or in the form of solutions, emulsions, suspensions and the like. In parenteral administration, they may be given in the form of injections.

In preparing such pharmaceutical preparations, the present compounds may be formulated using those additives conventionally used for formulation, such as excipients, stabilizers, preservatives, solubilizers, wetting agents, emulsions, lubricants, sweeteners, colorants, flavorings, tonicity agents, buffers, antioxidants and the like.

Route and dosage of administration for the present gastrointestinal prokinetic agent are not specifically limited and are appropriately chosen depending upon various dosage forms, sex of the patients, severity of the diseases. Daily dose of the active ingredient is 0.001 mg to 1000 mg.

BEST MODE FOR CARRYING OUT THE INVENTION

This invention will be explained in greater detail by way of the following Preparation Examples and Examples. However, it is to be noted that Preparation Examples are given to explain the synthetic examples in regard to the starting compounds to be used for preparing the present compounds, while the Examples are given for explaining the synthesis and use of this invention as medicines. Those Preparation Examples and Examples are given simply for the purpose of explaining this invention and it is not to be construed that they are limiting this invention.

Preparation Example 1

2-Benzylamino-2-methylthio-1,1-ethylenedicarbonitrile

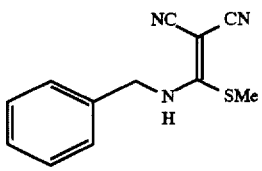

To a solution of malononitrile (1.21 g, 18.3 mmol) in DMF (40 ml) was added under ice-cooling sodium hydride (0.77 g, 19.2 mmol). After stirring for one hour, benzyl isothiocyanate (2.73 g, 18.3 mmol) was added dropwise. After stirring under ice-cooling for 1.5 hours, methyl iodide (2.60 g, 18.3 mmol) was added dropwise. After stirring at room temperature for 15 hours, water (400 ml) was added to the reaction mixture, which was then extracted with ethyl acetate (100 ml×2). The organic layer was washed with a saturated aqueous solution of sodium chloride, dried over sodium sulfate and concentrated under reduced pressure. The residue was purified by silica gel column chromatography to give the title compound as a yellow oily substance (2.94 g) from the fraction from hexane-ethyl acetate (2/1). Yield=70%.

$^1$HNMR(CDCl$_3$) δ2.63(s,3H), 4.71(d,J=6 Hz,2H), 6.82 (bs,1H), 7.22–7.42(m,5H)

IR(film) 3204, 2190, 1727, 1638, 1561, 1408, 1235, 1045, 735 cm$^{-1}$

MS m/z 229(M$^+$)

Preparation Example 2

2-Methylamino-2-methylthio-1,1-ethylenedicarbonitrile

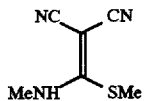

This compound was synthesized from malononitrile and methyl isothiocyanate according to the same process as in Preparation Example 1. Yield=43%.

m.p. 118°–121° C. (recrystallized from hexane-ethyl acetate) $^1$HNMR(CDCl$_3$) δ2.68 (s,3H), 3.22(d,J=5 Hz,3H), 6.28(bs,1H) IR(KBr) 3318, 2208, 2186, 1548, 1403, 1285 cm$^{-1}$ MS m/z 153(M$^+$)

Preparation Example 3

2-Phenylamino-2-methylthio-1,1-ethylenedicarbonitrile

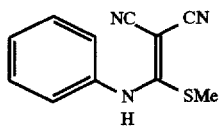

This compound was synthesized from malononitrile, phenyl isothiocyanate and methyl iodide according to the same process as in Preparation Example 1. Yield=66%.

m.p. 170°–176° C. (recrystallized from ethanol)

$^1$HNMR(CDCl$_3$) δ2.29(s,3H), 7.26–7.29(m,2H), 7.31–7.36(m,1H), 7.41–7.46(m,2H), 7.86(bs,1H)

IR(KBr) 3292, 2208, 2198, 2184, 1597, 1526, 1494, 1451, 1265, 968, 761, 701 cm$^{-1}$

MS m/z 215(M$^+$)

Preparation Example 4

2Cyclohexylamino-2-methylthio-1,1-ethylenedicarbonitrile

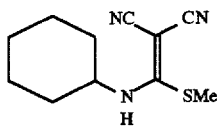

This compound was synthesized from malononitrile, cyclohexyl isothiocyanate and methyl iodide according to the same process as in Preparation Example 1. Yield=99%.

m.p. 102°–103° C. (recrystallized from hexane-ethyl acetate)

$^1$HNMR(CDCl$_3$) δ1.21–1.41(m,5H), 1.64–1.68(m,1H), 1.78–1.83(m,2H), 1.97–2.00(m,2H), 2.68(s,3H), 3.86–3.94 (m,1H), 5.99(bs,1H)

IR(KBr) 3252, 2936, 2210, 2192, 1568, 1562, 1422, 1357, 732 cm$^{-1}$

MS m/z 221(M$^+$)

Preparation Example 5

2-Isobutylamino-2-methylthio-1,1-ethylenedicarbonitrile

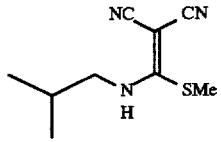

This compound was synthesized as a yellow oily substance from malononitrile, isobutyl isothiocyanate and methyl iodide according to the same process as in Preparation Example 1. Yield=91%.

$^1$HNMR(CDCl$_3$) δ0.98(d,J=7 Hz,6H), 1.85–1.96(m,1H), 2.67(s,3H), 3.38(t,J=6 Hz,2H), 6.49(bs,1H)

IR(film) 3242, 2962, 2210, 1562, 1373, 1271cm$^{-1}$

MS m/z 195(M$^+$)

Preparation Example 6

Ethyl 3-cyclohexylamino-3-methylthio-2-cyanoacrylate

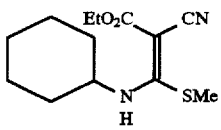

To a solution of ethyl cyanoacetate (2.07 g, 18.3 mmol) in DMF (40 ml) was added under ice-cooling sodium hydride (0.77 g, 19.2 mmol). After stirring for one hour, cyclohexyl isothiocyanate (2.59 g, 18.3 mmol) was added dropwise. After stirring under ice-cooling for 1.5 hours, methyl iodide (2.60 g, 18.3 mmol) was added dropwise. After stirring at room temperature for 15 hours, water (400 ml) was added to the reaction mixture, which was then extracted with ethyl acetate (100 ml×2). The organic layer was washed with a saturated aqueous solution of sodium chloride, dried over sodium sulfate and concentrated under reduced pressure. The residue was purified by silica gel column chromatography to give the title compound as a yellow oily substance (4.76 g) from the fraction from hexane-ethyl acetate (4/1). Yield=97%.

$^1$HNMR(CDCl$_3$) δ1.24–1.41(m,5H), 1.32(t,J=7 Hz,3H), 1.61–1.64(m,1H), 1.75–1.78(m,2H), 1.90–1.93(m,2H), 2.70 (s,3H), 3.93–3.96(m,1H), 4.21(q,J=7 Hz,2H), 10.10(bs,1H)

IR(KBr) 2932, 2856, 2206, 1656, 1563, 1259, 1143, 1031, 783 cm$^{-1}$

MS m/z 268(M$^+$)

Preparation Example 7

Ethyl 2-cyano-3-methylamino-3-methylthioacrylate

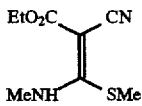

This compound was synthesized from ethyl cyanoacetate, methyl isothiocyanate and methyl iodide according to the same process as in Preparation Example 6. Yield=98%.

m.p. 87°–88° C. (recrystallized from hexane-ethyl acetate)

$^1$HNMR(CDCl$_3$) δ1.32(t,J=7 Hz,3H), 2.68(s,3H), 3.20(d, J=5 Hz,3H),4.21(q,J=7 Hz,2H), 10.00(bs,1H)

IR(KBr) 2200, 1650, 1587, 1382, 1266, 1031, 775 cm$^{-1}$

MS m/z 200(M$^+$)

Preparation Example 8

Ethyl 2-cyano-3-phenylamino-3-methylthioacrylate

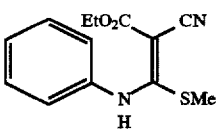

This compound was synthesized from ethyl cyanoacetate, phenyl isothiocyanate and methyl iodide according to the same process as in Preparation Example 6. Yield=68%.

m.p. 70°–71° C. (recrystallized from hexane-ethyl acetate)

$^1$HNMR(CDCl$_3$) δ1.35(t,J=7 Hz,3H), 2.23(s,3H), 4.26(q, J=7 Hz,2H),7.29–7.32(m,3H), 7.38–7.43(m,2H), 11.51(bs, 1H)

IR(KBr) 2204, 1656, 1561, 1377, 1265, 1027, 767cm$^{-1}$

MS m/z 263(M$^+$)

Preparation Example 9

Ethyl 2-cyano-3-isobutylamino-3-methylthioacrylate

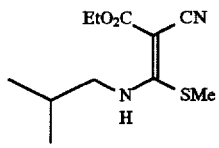

This compound was synthesized as a yellow oily substance from ethyl cyanoacetate, isobutyl isothiocyanate and methyl iodide according to the same process as in Preparation Example 6. Yield=80%.

$^1$HNMR(CDCl$_3$) δ0.98(d,J=7 Hz,6H), 1.33(t,J=7 Hz,3H), 1.82–1.96(m,1H), 2.67(s,3H), 3.42(t,J=7 Hz,2H), 4.22(q, J=7 Hz,2H), 10.17(bs,1H)

IR(KBr) 2874, 2206, 1655, 1573, 1400, 1383, 1270, 1188, 1137, 784cm$^{-1}$

MS m/z 242(M$^+$)

Preparation Example 10

Ethyl 3-benzylamino-2-cyano-3-methylthioacrylate

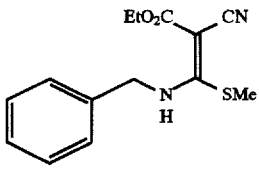

This compound was synthesized from ethyl cyanoacetate, benzyl isothiocyanate and methyl iodide according to the same process as in Preparation Example 6. Yield=61%.

m.p. 61°–62° C. (recrystallized from hexane-ethyl acetate)

$^1$HNMR(CDCl$_3$) δ1.31(t,J=7 Hz,3H), 2.65(s,3H), 4.20(q, J=7 Hz,2H), 4.77(d,J=6 Hz,2H), 7.23–7.39(m,5H), 10.39 (bs,1H)

IR(KBr) 3176, 2206, 1674, 1544, 1401, 1264, 1246, 1195, 742 cm$^{-1}$

MS m/z 276(M$^+$)

Preparation Example 11

Ethyl 2-cyano-3-(p-methoxyphenyl)amino-3-methylthioacrylate

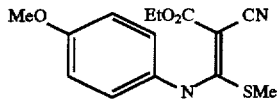

This compound was synthesized from ethyl cyanoacetate, p-methoxyphenyl isothiocyanate and methyl iodide according to the same process as in Preparation Example 6.

m.p. 83°–85° C. (recrystallized from hexane-ethyl acetate)

$^1$HNMR(CDCl$_3$) δ1.35(t,J=7 Hz,3H), 2.27(s,3H), 3.83(s, 3H), 4.26(q,J=7 Hz,2H), 6.91(d,J=9 Hz,2H), 7.19(d,J=9 Hz,2H), 11.42(bs,1H)

IR(KBr) 3122, 2208, 1667, 1611, 1540, 1509, 1378, 1263, 1245, 1168, 1018, 781cm$^{-1}$

MS m/z 292(M$^+$)

EXAMPLE 1

2-Benzylamino-2-[4-(p-fluorobenzyl)-2-morpholinylmethylamino]-1,1-ethylenedicarbonitrile

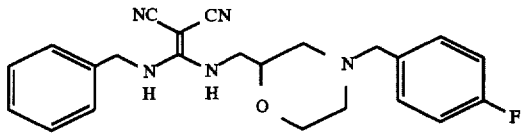

To a solution of 2-benzylamino-2-methylthio-1,1-ethylenedicarbonitrile (0.80 g, 3.49 mmol) in acetonitrile (20 ml) was added 2-aminomethyl-4-(p-fluorobenzyl)morpholine (1.17 g, 5.23 mmol) and the mixture was stirred at room temperature for 8 hours. The reaction mixture was concentrated under reduced pressure and the residue was purified by silica gel column chromatography to give the title compound as a yellow oily substance (0.90 g) from the fraction from hexane-ethyl acetate (1/1). Yield=64%.

$^1$HNMR(CDCl$_3$) δ1.88(t,J=11 Hz,1H), 2.02–2.08(m,1H), 2.61(t,J=10 Hz,2H), 3.16–3.23(m,1H), 3.29–3.35(m,1H), 3.42(d,J=13 Hz,1H), 3.46(d,J=13 Hz,1H), 3.54–3.60(m,2H), 3.67(dd,J=2 Hz,11 Hz,1H), 4.53–4.62(m,2H), 6.02(bs,1H), 6.98–7.04(m,2H), 7.14(bs,1H), 7.23–7.41(m,6H)

MS m/z 405(M$^+$)

To a solution of the title compound (0.50 g) in ethanol (10 ml) was added under ice-cooling while stirring a solution of 4N hydrochloric acid-ethyl acetate (0.3 ml). The reaction mixture was concentrated under reduced pressure to give the corresponding hydrochloride (0.40 g) as a yellow amorphous.

m.p. 112°–114° C.

IR(KBr) 3300, 2202, 2176, 1562, 1515, 1229, 700 cm$^{-1}$

EXAMPLE 2

2-Cyclohexylamino-2-[4-(p-fluorobenzyl)-2-morpholinylmethylamino]-1,1-ethylenedicarbonitrile

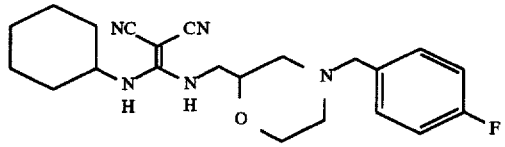

This compound was synthesized as a yellow oily substance from 2-cyclohexylamino-2-methylthio-1,1-ethylenedicarbonitrile and 2-aminomethyl-4-(p-fluorobenzyl)morpholine according to the same procedure as in Example 1. Yield=27%.

$^1$HNMR(CDCl$_3$) δ1.21–1.28(m,4H), 1.35–1.44(m,2H), 1.59–1.72(m,4H), 1.91–2.00(m,3H), 2.14(dt,J=3 Hz,11 Hz,1H), 2.63–2.69(m,2H), 3.29–3.34(m,1H), 3.43(d,J=13 Hz,1H), 3.47(d,J=13 Hz,1H), 3.62–3.74(m,2H), 3.84–3.91 (m,1H), 6.98–7.04(m,2H), 7.25–7.29(m,2H)

MS m/z 397(M$^+$)

Then, the corresponding hydrochloride was prepared in a conventional manner.

m.p. 128°–132° C.

IR(KBr) 3240, 2930, 2200, 2174, 1515, 1228 cm$^{-1}$

EXAMPLE 3

2-[4-(p-Fluorobenzyl)-2-morpholinylmethylamino]-2-phenylamino-1,1-ethylenedicarbonitrile

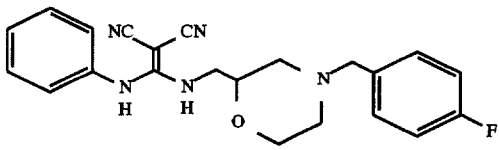

This compound was synthesized from 2-phenylamino-2-methylthio-1,1-ethylenedicarbonitrile and 2-aminomethyl-4-(p-fluorobenzyl)morpholine according to the same procedure as in Example 1. Yield=61%.

m.p. 65°–67° C. (a foamy solid)

$^1$HNMR(CDCl$_3$) δ1.95(t,J=11 Hz,1H), 2.18(dt,J=3 Hz,12 Hz,1H), 2.65–2.70(m,2H), 3.25–3.31(m,2H), 3.40–3.52(m, 3H), 3.67–3.75(m,2H), 3.54(d,J=10 Hz,1H), 6.24(bs,1H), 7.00–7.04(m,2H), 7.10(d,J=8 Hz,2H), 7.20–7.29(m,3H), 7.36–7.40(m,2H), 8.36(bs,1H)

IR(KBr) 3258, 2206, 2182, 1607, 1588, 1510, 1222, 692 cm$^{-1}$

MS m/z 391(M$^+$)

EXAMPLE 4

2-[4-(p-fluorobenzyl)-2-morpholinylmethylamino]-2-methylamino-1,1-ethylenedicarbonitrile

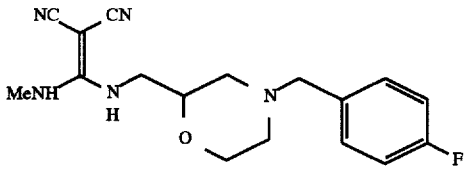

This compound was synthesized from 2-methylamino-2-methylthio-1,1-ethylenedicarbonitrile and 2-aminomethyl-4-(p-fluorobenzyl)morpholine according to the same procedure as in Example 1. Yield=87%.

m.p. 143°–144° C. (recrystallized from ethanol)

$^1$HNMR(CDCl$_3$) δ1.93(t,J=10 Hz,1H), 2.17(dt,J=3 Hz,11 Hz,1H), 2.67(t,J=10 Hz,2H), 3.08(d,J=5 Hz,3H), 3.17–3.24 (m,1H), 3.30–3.36(m,1H), 3.46(d,J=13 Hz,1H), 3.51(d,J=13 Hz,1H), 3.62–3.66(m,1H), 3.71(dt,J=2 Hz,11 Hz,1H), 3.92 (dd,J=2 Hz,11 Hz,1H), 5.70(t,J=5 Hz,1H), 6.69(bs,1H), 6.99–7.05(m,2H), 7.23–7.30(m,2H)

IR(KBr) 3294, 2870, 2204, 2174, 1603, 1586, 1509, 1221, 1058, 845 cm$^{-1}$

MS m/z 329(M$^+$)

EXAMPLE 5

2-Cyclohexylamino-2-[4-(p-fluorobenzyl)-1-piperazinyl]-1,1-ethylenedicarbonitrile

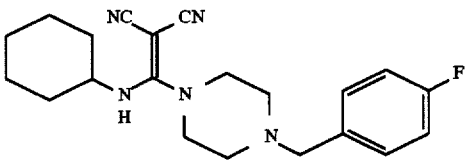

This compound was synthesized from 2-cyclohexylamino-2-methylthio-1,1-ethylenedicarbonitrile and 1-(p-fluorobenzyl)piperazine according to the same procedure as in Example 1. Yield=47%.

m.p. 145°–147° C. (a foamy solid) $^1$HNMR(CDCl$_3$) δ1.24–1.39(m,5H), 1.59–1.75(m,5H), 2.54(t,J=5 Hz,4H), 3.41(t,J=5 Hz,4H), 3.50(s,2H), 3.79–3.80(m,1H), 6.98–7.02 (m,2H), 7.26–7.29(m,2H)

IR(KBr) 3284, 2922, 2850, 2188, 1560, 1487, 1448, 1220, 1007, 808 cm$^{-1}$

MS m/z 367(M$^+$)

EXAMPLE 6

2-Benzylamino-2-[4-(p-fluorobenzyl)-1-piperazinyl]-1,1-ethylenedicarbonitrile

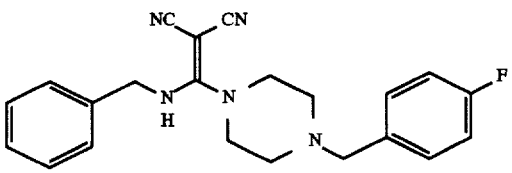

This compound was synthesized as a yellow amorphous from 2-benzylamino-2-methylthio-1,1-ethylenedicarbonitrile and 1-(p-fluorobenzyl)piperazine according to the same procedure as in Example 1. Yield=61%.

$^1$HNMR(CDCl$_3$) δ2.51(t,J=5 Hz,4H), 3.45(t,J=5 Hz,4H), 3.49(s,2H),4.41(d,J=5 Hz,2H), 5.04(t,J=5 Hz,1H), 6.97–7.03(m,2H), 7.24–7.30(m,4H), 7.33–7.42(m,3H)

IR(KBr) 3248, 2204, 2182, 1562, 1510, 1222, 1001, 699 cm$^{-1}$

MS m/z 375(M$^+$)

EXAMPLE 7

2-[4-(p-Fluorobenzyl)-2-morpholinylmethylamino]-2-isobutylamino-1,1-ethylenedicarbonitrile

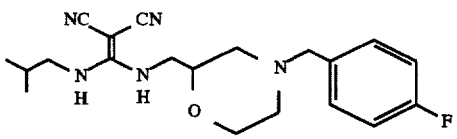

This compound was synthesized as a yellow oily substance from 2-isobutylamino-2-methylthio-1,1-ethylenedicarbonitrile and 2-aminomethyl-4-(p-fluorobenzyl)-morpholine according to the same procedure as in Example 1. Yield=48%.

$^1$HNMR(CDCl$_3$)δ0.97(d,J=7 Hz,6H), 1.82–1.92(m,1H), 1.95(t,J=11 Hz,1H), 2.15(dt,J=3 Hz,12 Hz,1H), 2.67(d,J=12 Hz,2H), 3.17–3.35(m,4H),3.47(d,J=13 Hz,1H), 3.51(d,J=13 Hz,1H), 3.62–3.66(m,1H), 3.71(dt,J=2 Hz,11 Hz,1H), 3.88 (dd,J=2 Hz,11 Hz,1H), 5.96(t,J=6 Hz,1H), 7.00–7.05(m, 2H), 7.26–7.29(m,2H)

IR(KBr) 3310, 2960, 2202, 2176, 1575, 1516, 1230, 1092, 845 cm$^{-1}$

MS m/z 371(M$^+$)

Then, the corresponding hydrochloride was prepared in a conventional manner.

m.p. 110°–114° C.

EXAMPLE 8

Ethyl 3-benzylamino-3-[4-(p-fluorobenzyl)-2-morpholinylmethylamino]-2-cyanoacrylate

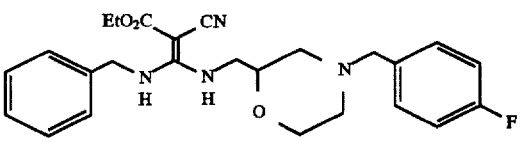

To a solution of ethyl 3-benzylamino-3-methylthio-2-cyanoacrylate (1.07 g, 3.87 mmol) in acetonitrile (10 ml) was added 2-aminomethyl-4-(p-fluorobenzyl)morpholine (0.90 g, 4.02 mmol) and the mixture was stirred at room temperature for 10 hours. The reaction mixture was concentrated under reduced pressure and the residue was purified by silica gel column chromatography to give the title compound as white crystals (0.70 g) from the fraction from hexane-ethyl acetate (1/1). Yield=40%.

m.p. 107°–108° C. (recrystallized from hexane-ethyl acetate)

$^1$HNMR(CDCl$_3$) δ1.30(t,J=7 Hz,3H), 1.86(t,J=11 Hz,1H), 2.08(dd,J=3 Hz, 12 Hz,1H), 2.59(d,J=11 Hz,2H), 3.27(bs,1H), 3.37–3.46(br,1H),3.38(d,J=13 Hz,1H), 3.45(d,

J=13 Hz,1H), 3.53–3.59(m,2H), 3.70(d,J=11 Hz,1H), 4.18 (q,J=7 Hz,2H), 4.58(bs,2H), 6.97–7.02(m,2H), 7.22–7.39 (m,7H)

IR(KBr) 3220, 2192, 1657, 1604, 1515, 1288, 1228, 1123, 1096, 775 cm$^{-1}$

MS m/z 452(M$^+$)

Then, the corresponding hydrochloride was prepared in a conventional manner.

m.p. 103°–107° C.

EXAMPLE 9

Ethyl 3-[4-(p-fluorobenzyl)-2-morpholinylmethylamino]-3-phenylamino-2-cyanoacrylate

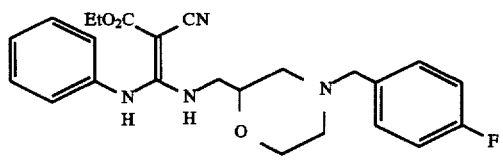

This compound was synthesized from ethyl 3-phenylamino-3-methylthio-2-cyanoacrylate and 2-aminomethyl-4-(p-fluorobenzyl)morpholine according to the same procedure as in Example 8. Yield=66%.

m.p. 114°–1160° C.

$^1$HNMR(CD$_3$OD) δ1.26(bs,3H), 1.89(t,J=11 Hz, 1H), 2.19(t,J=11 Hz,1H), 2.65(m,2H), 3.15–3.24(m,2H), 3.45(d, J=13 Hz,1H), 3.50(d,J=13 Hz,1H), 3.66(bs,2H), 3.91(d,J=11 Hz,1H), 4.14(bs,2H), 7.02–7.33(m,9H)

IR(KBr) 3168, 2482, 2200, 1654, 1612, 1516, 1455, 1285, 1113, 1096, 771, 751, 696 cm$^{-1}$

MS m/z 438(M$^+$)

Then, the corresponding hydrochloride was prepared in a conventional manner.

m.p. 174°–179° C.

EXAMPLE 10

Ethyl 3-[4-(p-fluorobenzyl)-2-morpholinylmethylamino]-3-isobutylamino-2-cyanoacrylate

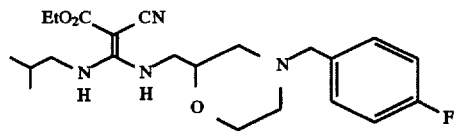

This compound was synthesized as a yellow oily substance from ethyl 3-isobutylamino-3-methylthio-2-cyanoacrylate and 2-aminomethyl-4-(p-fluorobenzyl) morpholine according to the same procedure as in Example 8. Yield=22%.

$^1$HNMR(CDCl$_3$) δ0.98(d,J=7 Hz,6H), 1.29(t,J=7 Hz,3H), 1.82–1.90(m,1H), 1.96(t,J=11 Hz,1H), 2.17(dt,J=3 Hz,12 Hz,1H), 2.66(d,J=11 Hz,2H), 3.15–3.42(m,4H), 3.43(d,J=13 Hz,1H), 3.50(d,J=13 Hz,1H), 3.64–3.73(m,2H), 3.90(dd,J=2 Hz,11 Hz,1H), 4.16(q,J=7 Hz,2H), 6.98–7.03(m,2H), 7.25–7.29(m,2H)

IR(film) 3254, 2960, 2190, 1656, 1605, 1569, 1517, 1288, 1232,1112, 776 cm$^{-1}$ MS m/z 418(M$^+$)

Then, the corresponding hydrochloride was prepared in a conventional manner.

m.p. 133°–136° C.

EXAMPLE 11

Ethyl 3-cyclohexylamino-3-[4-(p-fluorobenzyl)-2-morpholinylmethylamino]-2-cyanoacrylate

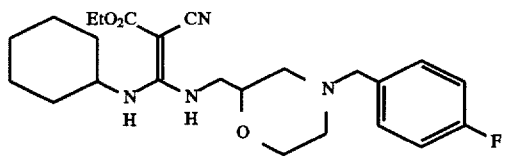

This compound was synthesized as a yellow oily substance from ethyl 3-cyclohexylamino-3-methylthio-2-cyanoacrylate and 2-aminomethyl-4-(p-fluorobenzyl) morpholine according to the same procedure as in Example 8. Yield=10%.

$^1$HNMR(CDCl$_3$) δ1.22–1.31(m,6H), 1.28(t,J=7 Hz,3H), 1.35–1.44(m,2H), 1.58–1.61(m,1H), 1.70–1.73(m,2H), 1.98–1.93(m,3H), 2.17(dt,J=3 Hz,11 Hz,1H), 2.66(d,J=11 Hz,2H), 3.27(bs,1H), 3.40(bs,1H), 3.44(d,J=13 Hz,1H), 3.50(d,J=13 Hz,1H), 3.67–3.72(m,2H), 3.90(dd,J=2 Hz,11 Hz,1H), 4.16(q,J=7 Hz,2H), 6.98–7.03(m,2H), 7.25–7.29 (m,2H)

IR(film) 3228, 2856, 2190, 1656, 1605, 1515, 1287, 1228, 1124, 1094, 77 cm$^{-1}$ MS m/z 444(M$^+$)

Then, the corresponding hydrochloride was prepared in a conventional manner.

m.p. 105°–113° C.

EXAMPLE 12

Ethyl 3-[4-(p-fluorobenzyl)-2-morpholinylmethylamino]-3-(p-methoxybenzyl)amino-2-cyanoacrylate

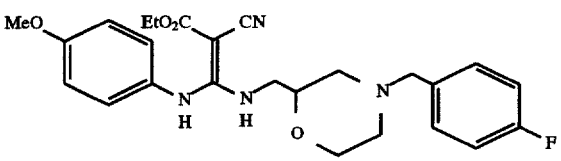

This compound was synthesized from ethyl 3-(p-methoxyphenyl)amino-3-methylthio-2-cyanoacrylate and 2-aminomethyl-4-(p-fluorobenzyl)morpholine according to the same procedure as in Example 8. Yield=71%.

m.p. 131°–133° C.

$^1$HNMR(DMSO-d$_6$) 61.18(t,J=7 Hz,3H), 1.79(t,J=11 Hz,1H), 2.08(dt,J=3 Hz,11 Hz,1H), 2.59(d,J=11 Hz,2H), 3.12–3.27(m,2H), 3.34(s,3H), 3.39(d,J=13 Hz,1H), 3.47(d, J=13 Hz,1H), 3.50–3.57(m,2H), 3.82(d,J=11 Hz,1H), 4.05 (q,J=7 Hz,2H), 6.88(d,J=9 Hz,2H), 7.00(d,J=9 Hz,2H), 7.10–7.14(m,2H), 7.29–7.33(m,2H)

IR(KBr) 3240, 2932, 2196, 1656, 1615, 1513, 1250, 1239, 1220, 1117, 1142, 825 cm$^{-1}$

MS m/z 468(M$^+$)

Then, the corresponding hydrochloride was prepared in a conventional manner.

m.p. 125°–131° C.

EXAMPLE 13

Ethyl 3-[4-(p-fluorobenzyl)-2-morpholinylmethylamino]-3-methylamino-2-cyanoacrylate

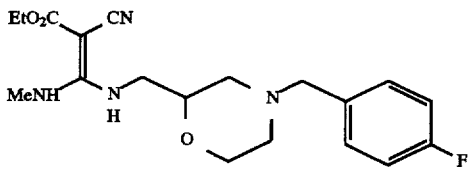

This compound was synthesized as a yellow oily substance from ethyl 3-methylamino-3-methylthio-2-cyanoacrylate and 2-aminomethyl-4-(p-fluorobenzyl)morpholine according to the same procedure as in Example 8. Yield=53%.

$^1$HNMR(CDCl$_3$) δ1.30(t,J=7 Hz,3H), 1.95(t,J=11 Hz,1H), 2.17(dt,J=3 Hz,11 Hz,1H), 2.65(d,J=11 Hz,2H), 3.06(bs,3H), 3.23–3.55(m,2H), 3.43(d,J=13 Hz,1H), 3.50(d, J=13 Hz,1H), 3.66–3.73(m,2H), 3.91(dd,J=2 Hz,11 Hz,1H), 4.17(q,J=7 Hz,2H), 6.99–7.03(m,2H), 7.29–7.50(m,2H)

IR(film) 3232, 2186, 1738 cm$^{-1}$

MS m/z 376(M+)

EXAMPLE 14

Ethyl 3-cyclohexylamino-3-[7-(p-fluorophenyl)-6-aza-3-oxaheptylamino]-2-cyanoacrylate

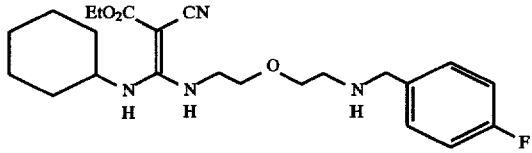

a) Synthesis of ethyl 3-[6-(tert-butyloxycarbonyl)-7-(p-fluorophenyl)-6-aza-3-oxaheptylmethyl]-3-cyclohexylamino-2-cyanoacrylate To a solution of ethyl 3-cyclohexylamino-3-methylthio-2-cyanoacrylate (1.50 g, 5.60 mmol) in acetonitrile (10 ml) was added tert-butoxy N-(5-amino-3-oxapentyl)-N-(p-fluorobenzyl)carbamate (3.10 g, 11.2 mmol) and the mixture was stirred at room temperature for 18 hours. The reaction mixture was concentrated and the residue was purified by silica gel column chromatography to give the title compound as a pale yellow oily substance (1.72 g) from the fraction from hexane-ethyl acetate (2/1). Yield=58%.

$^1$HNMR(CDCl$_3$) δ1.16–1.44(m,4H), 1.29(t,J=7 Hz,3H), 1.44(bs,9H),1.58–1.64(m,2H), 1.70–1.72(m,2H), 1.94–2.04 (m,2H), 3.33–3.55(m,8H), 4.16(q,J=7 Hz,2H), 4.43(bs,2H), 6.99–7.04(m,2H), 7.19(bs, 2H)

IR(film) 3308, 2932, 2193, 1607, 1513 cm$^{-1}$ b) Synthesis of ethyl 3-cyclohexylamino-3-[7-(p-fluorophenyl)-6-aza-3-oxaheptylamino]-2-cyanoacrylate To a solution of ethyl 3-[6-(tert-butyloxycarbonyl)-7-(p-fluorophenyl)-6-aza-3-oxaheptylmethyl]-3-cyclohexylamino-2-cyanoacrylate (1.72 g, 3.23 mmol) in methanol (15 ml) was added a 4N hydrochloric acid-ethyl acetate solution (2.5 ml) and the mixture was stirred at room temperature for 14 hours. The reaction mixture was concentrated and water (50 ml) was added to the residue. The mixture was adjusted to pH 12 with an aqueous solution of sodium hydroxide and extracted with chloroform (50 ml×3). The organic layer was dried over sodium sulfate and the solvent was distilled off under reduced pressure. The residue was purified by silica gel column chromatography to give the title compound as a yellow oily substance (1.06 g) from the fraction from chloroform-methanol-aqueous ammonia (30/1/0.05). Yield=76%.

$^1$HNMR(CDCl$_3$) δ1.23–1.40(m,8H), 1.58–1.61(m,1H), 1.70–1.75(m,4H), 1.95–1.98(m,2H), 2.81(t,J=5 Hz,2H), 3.58–3.65(m,5H), 3.78(s,2H), 4.13(q,J=7 Hz,2H), 6.99–7.03 (m,2H), 7.26–7.31(m,2H)

IR(film) 3222, 2856, 2190, 1649, 1223, 778 cm$^{31}$ $^1$

MS m/z 432(M$^+$)

Then, the corresponding hydrochloride was prepared in a conventional manner (a colorless and high viscous oil).

EXAMPLE 15

Ethyl 3-benzylamino-3-[4-(p-fluorobenzyl)-1-piperazinyl]-2-cyanoacrylate

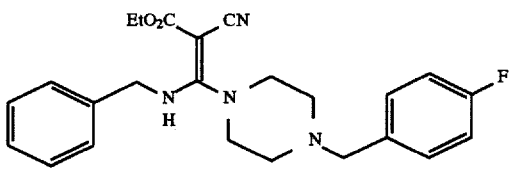

To ethyl 3-benzylamino-3-methylthio-2-cyanoacrylate (1.50 g, 5.43 mmol) and 1-(p-fluorobenzyl)piperazine (2.11 g, 10.9 mmol) was added acetonitrile (1 ml) and the mixture was heated under reflux at 80° C. for 2 hours. The reaction product was purified by silica gel column chromatography to give the title compound as a brown oily substance (0.48 g) from the fraction from hexane-ethyl acetate (1/1). Yield= 21%.

$^1$HNMR(CDCl$_3$) 61.29(t,J=7 Hz,3H), 2.50(bs,4H), 3.37 (bs,4H), 3.47(s,2H), 4.18(q,J=7 Hz,2H), 4.35(d,J=6 Hz,2H), 6.97–7.01(m,2H),7.24–7.37(m,7H), 8.46(bs,1H)

IR(film) 3266, 2938, 2196, 1658, 1512, 1134, 756 cm$^{-1}$

MS m/z 422(M$^+$)

EXAMPLE 16

2-(p-Fluorobenzylamino)-2-[4-(p-fluorobenzyl)-2-morpholinylmethylamino]-1,1-ethylenedicarbonitrile

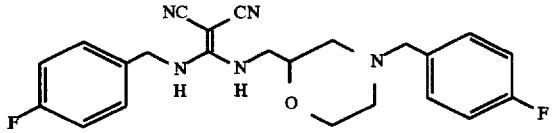

a) 2-[4-(p-Fluorobenzyl)-2-morpholinylmethylamino]-2-methylthio-1,1-ethylenedicarbonitrile

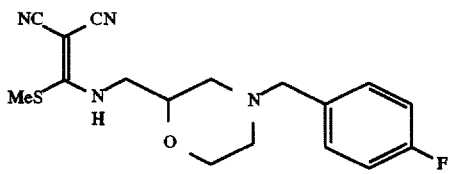

To a solution of 2-aminomethyl-4-(p-fluorobenzyl)-morpholine (500 mg, 2.23 mmol) in acetonitrile (10 ml) was added 2,2-dimethylthio-1,1-ethylenedicarbonitrile (417 mg, 2.46 mmol) and the mixture was stirred at room temperature for 2.5 hours. The reaction mixture was concentrated under reduced pressure and the residue was subjected to silica gel column chromatography to give the title compound (650 mg) from the fraction from ethyl acetate-hexane (2/1). Yield=84%.

¹HNMR(CDCl₃) δ1.92(t,J=10 Hz,1H), 2.21(dt,J=3 Hz,1H Hz,1H), 2.52–2.76(m,2H), 2.62(s,3H), 3.35–3.57(m,3H), 3.58–3.79(m,3H), 3.82–3.97(s,1H), 6.30–6.53(br,1H), 7.02 (t,J=8 Hz,2H), 7.15–7.36(m,2H) b) 2-(p-Fluorobenzylamino)-2-[4-(p-fluorobenzyl)-2-morpholinylmethylamino]-1,1-ethylenedicarbonitrile To a solution of 2-[4-(p-fluorobenzyl)-2-morpholinylmethylamino]-2-methylthio-1,1-ethylenedicarbo-nitrile (650 mg, 1.88 mmol) in acetonitrile (7 ml) was added p-fluorobenzylamine (0.24 ml, 2.1 mmol), and the mixture was heated under reflux for 13 hours. The reaction mixture was concentrated under reduced pressure to distill off the solvent and the residue was chromatographed using silica gel column to give the title compound (760 mg) as a pale yellow oily substance from the fraction from ethyl acetate-hexane (2/1). Yield=96%.

¹HNMR(CDCl₃) δ1.87(t,J=11.23 Hz,1H), 1.98–2.12(m, 1H), 2.51-2.68(m,2H), 3.11–3.23(m,1H), 3.23–3.36(m,1H), 3.42(d,J=12.7 Hz,1H), 3.48(d,J=13.19 Hz,1H), 3.51–3.73 (m,3H), 4.56(d,J=4.88 Hz,2H),5.62–5.78(brm,1H), 6.90–7.13(m,4H), 7.18–7.32(m,4H)

IR(film) 3300, 2205, 2180, 1600, 1580, 1505 cm⁻¹

EXAMPLE 17

Ethyl 2-cyano-3-[endo-9-(p-fluorobenzyl)-9-aza-3-oxabicyclo[3.3.1]non-7-ylamino]-3-methylaminoacrylate

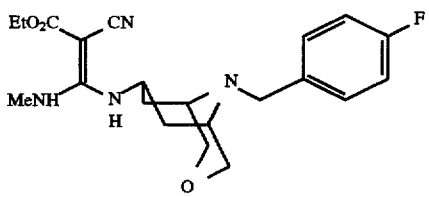

To a solution of endo-7-amino-9-(p-fluorobenzyl)-9-aza-3-oxabicyclo[3.3.1]nonane (280 mg, 0.979 mmol) in acetonitrile (5 ml) was added ethyl 2-cyano-3-methylamino-3-methylthioacrylate (249 mg, 1.27 mmol) and the mixture was stirred at room temperature for 1.5 hours and then heated under reflux for 8 hours. The reaction mixture was concentrated under reduced pressure and the residue was subjected to silica gel column chromatography to give the title compound (220 mg) from the fraction with ethyl acetate-hexane (1/1). Yield=52%.

¹HNMR(CDCl₃) δ1.29(t,J=7 Hz,3H), 1.54(d,J=16 Hz,2H), 2.41–2.58(m,2H), 2.65–2.80(m,2H), 2.85(d,J=5 Hz,3H), 3.79(d,J=14 Hz,4H), 3.98(d,J=11 Hz,2H), 4.17(q, J=7 Hz,2H), 4.73(bs,1H), 6.95–7.06(m,2H), 7.29(m,2H), 7.82(bs,1H), 9.00(bs,1H)

IR(KBr) 3275, 2200, 1645 cm⁻¹

EXAMPLE 18

2-[endo-9-(p-Fluorobenzyl)-9-aza-3-oxabicyclo [3.3.1]non-7-ylamino] -2-methylamino-1, 1-ethylenedicarbonitrile

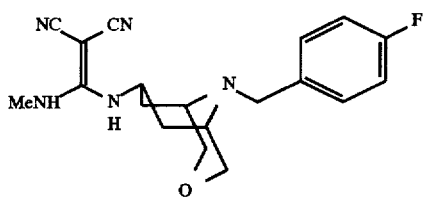

This compound was synthesized from endo-7-amino-9-(p-fluorobenzyl)-9-aza-3-oxabicyclo[3.3.1]nonane and 2-methylamino-2-methylthio-1,1-ethylenedicarbonitrile according to the same procedure as in Example 17. Yield=100%.

m.p. 226.5°–228° C.

¹HNMR(CDCl₃) δ1.42–1.72(m,4H), 1.40–1.60(m,2H), 2.65–2.80(br,2H), 2.86(d,J=5 Hz,3H), 3.76(d,J=9 Hz,2H), 3.99(d,J=11 Hz,2H), 3.41–3.63(br,1H), 5.23–5.42(br,1H), 7.01(t,J=8 Hz,2H), 7.18–7.47(m,2H), 8.13(d,J=11 Hz,1H)

IR(film) 2200, 2175, 1560 cm⁻¹

EXAMPLE 19

2-[endo-9-[3-(p-Fluorophenoxy)propyl]-9-aza-3-oxabicyclo-[3.3.1]non-7-ylamino]-2-methylamino-1, 1-ethylenedicarbonitrile

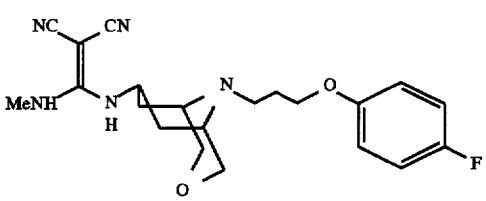

This compound was synthesized from 2-methylamino-2-methylthio-1,1-ethylenedicarbonitrile and endo-7-amino-9-[3-(p-fluorophenoxy)propyl]-9-aza-3-oxabicyclo[3.3.1] nonane according to the same procedure as in Example 17. Yield=32%.

m.p. 195°–196° C. (recrystallized from hexane-ethyl acetate) ¹HNMR(CDCl₃) δ1.52(d,J=16 Hz,2H), 1.86(dd,J=6 Hz,7 Hz,2H), 2.43–2.50(m,2H), 2.78–2.81(m,4H), 2.85(d, J=5 Hz,3H), 3.77(d,J=12 Hz, 2H), 3.96(d,J=11 Hz,2H), 3.99(t,J=6 Hz,2H), 4.46(bs,1H), 5.51(bs,1H), 6.80–6.85(m, 2H), 6.94–7.00(m,2H), 8.10(d,J=10 Hz,1H)

IR(KBr) 3282, 2200, 2176, 1559, 1509, 1428, 1386, 1338, 1247, 1205, 831 cm⁻¹

MS m/z 399(M⁺)

EXAMPLE 20

N-[endo-9-(p-Fluorobenzyl)-9-aza-3-oxabicyclo[3.3.1]non-7-yl]-N'-methyl-2-nitrovinylidene-1,1-diamine

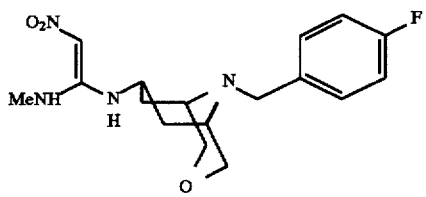

endo-7-Amino-9-aza-9-(p-fluorobenzyl)-3-oxabicyclo[3.3.1]nonane (1.55 g) and N-(1-methylthio-2-nitrovinyl)-N-methylamine (2.11 g) were heated at 80° C. for 2 hours. The reaction mixture was purified by silica gel column chromatography to give the title compound (0.65 g) from the fraction from chloroform-methanol-aqueous ammonia (20/1/0.5). Yield=30%.

m.p. 184°–186° C.

$^1$HNMR(CDCl$_3$) δ1.48(d,J=15 Hz,2H), 2.39–2.45(m, 2H), 2.73(bs,2H), 2.89(d,J=5 Hz,3H), 3.73(d,J=11 Hz,2H), 3.80(s,2H), 3.81–3.87(m,2H), 4.01(d,J=11 Hz,2H), 6.66(s, 1H), 6.99–7.05(m,2H), 7.30- 7.34(m,2H), 7.85(d,J=10 Hz,1H), 10.23(bs,1H)

IR(KBr) 2940, 1676, 1570, 1516, 1229, 1072, 924 cm$^{-1}$

To a solution of the title compound (0.63 g) in chloroform (10 ml) was added under ice-cooling a 4N hydrochloric acid-ethyl acetate solution (0.5 ml). The crystal thus separated out was recovered by filtration and dried under reduced pressure to give the corresponding hydrochloride (0.64 g).

m.p. 180° C. (dec.)

EXAMPLE 21

1-[4-(p-Fluorobenzyl)-2-morpholinylmethyl]-3-phenylurea

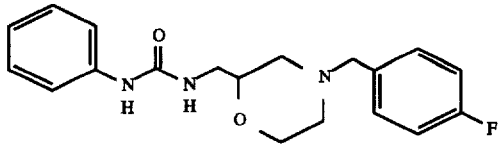

To a solution of 2-aminomethyl-4-(p-fluorobenzyl)-morpholine (1.0 g, 4.5 mmol) in dimethylformamide (10 ml) was added under ice-cooling phenyl isocyanate (0.53 ml, 4.9 mmol) and the mixture was stirred for 30 minutes. To the reaction mixture was added purified water (20 ml) and the crystals thus separated out were then recovered by filtration to give the title compound (1.1 g). Yield=72%.

$^1$HNMR(CDCl$_3$) δ1.93(t,J=11 Hz,1H,), 2.13(dt,J=3 Hz,12 Hz,1H,), 2.63(d,J=11 Hz,1H,), 2.70(d,J=11 Hz,1H), 3.10–3.22(m,1H), 3.38- 3.50(m,1H), 3.44(s,2H), 3.58–3.70 (m,2H), 3.84(dd,J=1 Hz,11 Hz,1H),5.10–5.23(br,1H), 6.70–6.89(br,1H), 6.94–7.14(m,3H), 7.19–7.39(m,6H)

IR(KBr) 3350, 1648, 1562, 1500, 1220 cm$^{-1}$

Then, the corresponding hydrochloride was prepared in a conventional manner.

m.p. 183°–187° C.

EXAMPLE 22

1-[4-(p-Fluorobenzyl)-2-morpholinylmethyl]-3-methylurea

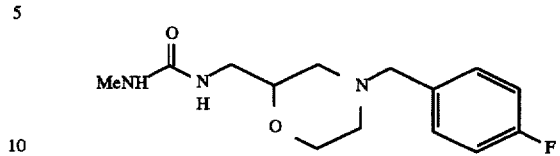

This compound was synthesized from 2-aminomethyl-4-(p-fluorobenzyl)morpholine and methyl isocyanate according to the same procedure as in Example 21. Yield=65%.

m.p. 164°–166° C.

$^1$HNMR(CDCl$_3$) δ1.90(t,J=11 Hz,1H), 2.12(dt,J=3 Hz,11 Hz,1H), 2.62(dd,J=1 Hz,11 Hz,1H), 2.69(dd,J=2 Hz,11 Hz,1H), 2.76(d,J=5 Hz,3H), 3.01–3.13(m,1H), 3.31–3.49 (m,1H), 3.44(s,2H), 3.52–3.61(m,2H), 3.75–3.90(m,1H), 4.50–4.82(br,2H), 7.00(t,J=9 Hz,2H), 7.18–7.34(m,2H)

IR(film) 3320, 1638, 1590 cm$^{-1}$

EXAMPLE 23

1-[endo-9-(p-Fluorobenzyl)-9-aza-3-oxabicyclo[3.3.1]non-7-yl]-3-methylurea

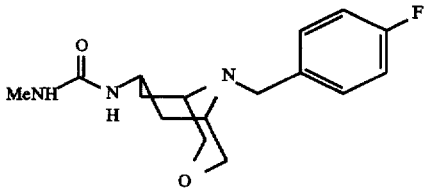

To a solution of endo-7-amino-9-(p-fluorobenzyl)-9-aza-3-oxabicyclo[3.3.1]nonane (670 mg, 2.34 mmol) in toluene (7 ml) was added under ice-cooling methyl isocyanate (0.15 ml, 2.6 mmol) and the mixture was stirred for 30 minutes. To the reaction mixture was added ethyl acetate (30 ml) and the mixture was washed with a 10% aqueous sodium hydroxide solution (20 ml), dried over potassium carbonate and the solvent was distilled off under reduced pressure. The residue was subjected to silica gel column chromatography to give the title compound (690 mg) from the fraction from methanol-chloroform (1/9). Yield=86%.

m.p. 167°–169° C.

$^1$HNMR(CDCl$_3$) δ1.41(d,J=15 Hz,2H), 2.31–2.44(m, 2H), 2.62(bs, 2H), 2.74(d,J=5 Hz,3H), 3.72(d,J=11 Hz,2H), 3.78(s,2H), 3.94(d,J=11 Hz,2H), 4.29–4.40(m,1H), 4.44–4.61(m,1H), 6.93–7.12(m,2H), 7.26–7.39(m,2H)

IR(film) 3375, 1645 cm$^{-1}$

EXAMPLE 24

Acetylcholine-release promoting action of the present compounds in the gastrointestinal tract was investigated according to the following procedure. A longitudinal muscle sample (including myenteric plexus) was prepared from the ileum excised from guinea pig and suspended in Magnus' tube. This sample was perfused in a physiological salt solution and stimulated by the electric current via platinum electrodes. Acetylcholine was released from the myenteric plexus of the sample by this stimulation and the longitudinal muscle was observed to contract. This contraction was isometrically recorded. Accordingly, the drug capable of accelerating the release of acetylcholine could enhance the contraction caused by electric stimulation only. Evaluation of the compounds was represented in terms of increase ratio in contraction by electrical stimulation. The tested compounds are shown in terms of the numbers of the corresponding Examples. The results are shown below.

| Example No. | Contraction increase rate (%) | |
|---|---|---|
| | $10^{-7}M$ | $10^{-5}M$ |
| 1 | 3.9 | 12.3 |
| 2 | | 5.3 |
| 7 | | 4.9 |
| 8 | 3.0 | 20.3 |
| 9 | 0.7 | |
| 10 | 8.5 | 32.4 |
| 11 | 8.7 | 31.9 |
| 12 | 9.1 | 11.8 |
| 14 | 0.8 | 7.9 |
| 16 | 4.9 | 15.0 |
| 18 | 3.9 | |
| 19 | 3.1 | |
| 21 | 3.2 | 5.7 |
| 22 | 9.8 | |
| 23 | 4.2 | |

Finally, illustrative examples of the pharmaceutical compositions which comprises as an active ingredient the present compound are given below by way of the following Examples.

EXAMPLE 25

(Formulation Example 1)

| Tablets (one tablet) | |
|---|---|
| The compound of Example 10 | 1 mg |
| Lactose | 70 mg |
| Crystalline cellulose | 20 mg |
| Corn starch | 8 mg |
| Magnesium stearate | 1 mg |
| Total | 100 mg |

All components were uniformly mixed to form a powder for direct compression. This powder was formed to tablets, each having a diameter of 6 mm and a weight of 100 mg.

(Formulation Example 2)

| Granules (one package) | | |
|---|---|---|
| A: | The compound of Example 11 | 1 mg |
| | Lactose | 99 mg |
| | Corn starch | 50 mg |
| | Crystalline cellulose | 50 mg |
| B: | Hydroxypropylcellulose | 10 mg |
| | Ethanol | 9 mg |

After all components of the above group A were uniformly mixed, the solution of the above group B was added. The mixture was kneaded, graded by an extrusion granulation method and then dried in a drier at 50° C. The granules as dried up was sieved to a grain size of 297 μm 1460 μm, thereby forming granules. One package comprised 200 mg.

(Formulation Example 3)

| Syrups | |
|---|---|
| The compound of Example 1 | 0.100 g |
| Sucrose | 30.000 g |
| D-Sorbitol 70 w/v % | 25.900 g |
| Ethyl para-hydroxybenzoate | 0.030 g |
| Propyl para-hydroxybenzoate | 0.015 g |
| Flavors | 0.200 g |
| Glycerol | 0.150 g |
| 96% Ethanol | 0.500 g |
| Distilled water | to make up a total volume to 100 ml |

The sucrose, D-sorbitol, ethyl para-hydroxybenzoate, propyl para-hydroxybenzoate and compound of Example 1 were dissolved in 60 g of hot water. After cooling, a solution of the flavors in the glycerol and ethanol was added. Then, the water was added to the resulting mixture to make up to a 100 ml volume.

INDUSTRIAL APPLICABILITY

The diaminomethylidene derivatives (I) or pharmacologically acceptable salts thereof as provided by the present invention can be applied for the therapy of digestive tract disorders derived from chronic gastritis, diabetes mellitus, post-gastrectomy and peptic ulcer and digestive tract diseases including reflux esophagitis, irritable bowel syndrome and spurious ileus, thus being useful as a gastrointestinal prokinetic agent.

We claim:

1. A diaminomethylidene derivative represented by formula (I)

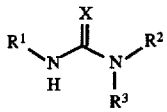

(I)

wherein $R^1$ is a hydrogen atom, a $C_1$–$C_6$ alkyl group, a $C_3$–$C_6$ cycloalkyl group, a $C_3$–$C_6$ cycloalkyl $C_1$–$C_1$ alkyl group, an aryl group or an aryl $C_1$–$C_4$ alkyl group, in which the aryl moiety of the aryl group or aryl $C_1$–$C_4$ alkyl group may be optionally substituted with a halogen atom, a $C_1$–$C_6$ alkyl group, a halo $C_1$–$C_6$ alkyl group, a $C_1$–$C_6$ alkoxy group, a $C_1$–$C_6$ alkoxycarbonyl group, a phenyl group or an amino group;

X is O, S, CHNO$_2$, C(COOR$^4$)$_2$, C(COOR$^4$)CN or C(CN)$_2$, in which $R^4$ is a $C_1$–$C_6$alkyl group, a $C_3$–$C_6$ cycloalkyl group, an aryl group, or an aryl $C_1$–$C_4$ alkyl group;

$R^2$ is a group of the following general formulae (II)–(III):

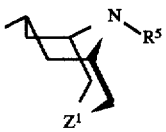

(II)

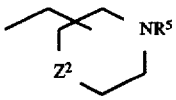

(III)

wherein $R^5$ is a $C_1$–$C_6$ alkyl group, an aryl $C_1$–$C_4$ alkyl group, or an aryloxy $C_2$–$C_6$ alkyl group, or in which the aryl moiety of the said groups may be optionally substituted with a halogen atom, a $C_1$–$C_6$ alkyl group, a halo $C_1$–$C_6$ alkyl group, a $C_1$–$C_6$ alkoxy group, a $C_1$–$C_6$ alkoxycarbonyl group, a phenyl group or an amino group;

$Z^1$ and $Z^2$ are O;

$R^3$ is a hydrogen atom, a $C_1$–$C_6$ alkyl group or a $C_1$–$C_6$ alkoxy $C_2$–$C_6$ alkyl group;

provided that there is excluded a compound wherein $R^1$ is an aryl group, X is O, and $R^2$ is a group of formula (II) wherein $R^5$ is a $C_1$–$C_2$ alkyl group or a pharmacologically acceptable salt thereof.

2. The compound of claim 1, represented by formula (I) wherein

X is O, S, CHNO$_2$, C(COOR$^4$)$_2$, C(COOR$^4$)CN, or C(CN)$_2$, in which $R^4$ is a $C_1$–$C_6$ alkyl group, a $C_3$–$C_6$ cycloalkyl group, a phenyl group, or a phenyl $C_1$–$C_4$ alkyl group; when X is O, $R^1$ is a $C_1$ is a $C_6$ alkyl group, when X is S, CHNO$_2$, C(COOR$^4$)$_2$, C(COOR$^4$)CN or C(CN)$_2$, $R^1$ is a hydrogen atom, a $C_1$–$C_6$ alkyl group, a $C_3$–$C_6$ cycloalkyl group, a phenyl group, a naphthyl group, a $C_3$–$C_6$ cycloalkyl $C_1$–$C_4$ alkyl group, or a phenyl $C_1$–$C_4$ alkyl group, in which the phenyl moiety of the phenyl group, naphthyl group or phenyl $C_1$–$C_4$ alkyl group may be optionally mono- to tri-substituted with a halogen atom, a $C_1$–$C_6$ alkyl group, a halo $C_{1-6}$ alkyl group, a $C_{1-6}$ alkoxy group, a $C_{1-6}$ alkoxycarbonyl group, or a phenyl group;

$R^2$ is a group of formula (II) wherein $R^5$ is a $C_1$–$C_6$ alkyl group, a phenyl $C_1$–$C_4$ alkyl group, a naphthyl $C_1$–$C_4$ alkyl group, or a phenoxy $C_2$–$C_6$ alkyl group, in which the phenyl, phenoxy or naphthyl moiety may be optionally mono- to tri-substituted with a halogen atom, a $C_1$–$C_6$ alkyl group, a halo $C_1$–$C_6$ alkyl group, a $C_1$–$C_6$ alkoxy group, a $C_1$–$C_6$ alkoxycarbonyl group, or a phenyl group, $Z^1$ is O;

$R^3$ is a hydrogen atom, a $C_1$–$C_6$ alkyl group or a $C_1$–$C_4$ alkoxy $C_2$–$C_4$ alkyl group or a pharmacologically acceptable salt thereof.

3. The compound of claim 1, represented by formula (I) wherein $R^1$ is a hydrogen atom, a $C_1$–$C_6$ alkyl group, a $C_3$–$C_6$ cycloalkyl group, a phenyl group, a naphthyl group, a $C_3$–$C_6$ cycloalkyl $C_1$–$C_4$ alkyl group, or a phenyl $C_1$–$C_4$ alkyl group, in which the phenyl moiety of the phenyl group, naphthyl group or phenyl $C_1$–$C_4$ alkyl group may be optionally mono- to tri-substituted with a halogen atom, a $C_1$–$C_6$ alkyl group, a halo $C_1$–$C_6$ alkyl group, a $C_1$–$C_6$ alkoxy group, a $C_1$–C6 alkoxycarbonyl group, or a phenyl group;

X is O, S, CHNO$_2$, C(COOR$^4$)$_2$, C(COOR$^4$)CN or C(CN)$_2$, in which $R^4$ is a $C_1$–$C_6$ alkyl group, a $C_3$–$C_6$ cycloalkyl group, a phenyl group, or a phenyl $C_1$–$C_4$ alkyl group;

$R^2$ is a group of formula (III) wherein $R^5$ is a $C_1$–$C_6$ alkyl group, a phenyl $C_1$–$C_4$ alkyl group, a naphthyl $C_1$–$C_4$ alkyl group, or a phenoxy $C_2$–$C_6$ alkyl group, in which the phenyl, phenoxy or naphthyl moiety may be optionally mono- to tri-substituted with a halogen atom, a $C_1$–$C_6$ alkyl group, a halo $C_1$–$C_6$ alkyl group, a $C_1$–$C_6$ alkoxy group, a $C_2$–$C_6$ alkoxycarbonyl group, or a phenyl group, $Z^2$ is O;

$R^3$ is a hydrogen atom, a $C_1$–$C_6$ alkyl group or a $C_1$–$C_4$ alkoxy $C_2$–$C_4$ alkyl group or a pharmacologically acceptable salt thereof.

4. A gastrointestinal prokinetic pharmaceutical composition which comprises as an active ingredient a compound represented by formula (I) as defined in claim 1 or a pharmacologically acceptable salt thereof, if necessary, in admixture with a pharmaceutically acceptable additive.

5. The gastrointestinal prokinetic pharmaceutical composition of claim 4, for use in the therapy of digestive tract disorders derived from chronic gastritis, diabetes mellitus, post-gastrectomy and peptic ulcer and digestive tract diseases including reflux esophagitis, irritable bowel syndrome with constipation as a chief complaint and spurious ileus.

* * * * *

UNITED STATES PATENT AND TRADEMARK OFFICE
CERTIFICATE OF CORRECTION

PATENT NO. : 5,753,654
DATED : May 19, 1998
INVENTOR(S) : Haruhiko KIKUCHI et al.

It is certified that error appears in the above-identified patent and that said Letters Patent is hereby corrected as shown below:

Column 26, line 42, "$C_1$-$C_1$ alkyl" should be --$C_1$-$C_4$ alkyl--;

Column 26, last line, "or" should be deleted;

Column 27, line 18, "$C_1$ is a $C_6$" should be --$C_1$-$C_6$--;

Column 28, line 10, "C6" should be --$C_6$--;

Column 28, line 22, "$C_2$-$C_6$" should be --$C_1$-$C_6$--.

Signed and Sealed this

Tenth Day of November 1998

*Attest:*

BRUCE LEHMAN

*Attesting Officer*     *Commissioner of Patents and Trademarks*